(12) United States Patent
Mitchell et al.

(10) Patent No.: US 9,350,319 B2
(45) Date of Patent: May 24, 2016

(54) SELF-POWERED SENSING AND TRANSMITTING DEVICE AND METHOD OF FABRICATING THE SAME

(71) Applicant: Siemens Energy, Inc., Orlando, FL (US)

(72) Inventors: David J. Mitchell, Oviedo, FL (US);
Anand A. Kulkarni, Charlotte, NC (US)

(73) Assignee: SIEMENS ENERGY, INC., Orlando, FL (US)

( * ) Notice: Subject to any disclaimer, the term of this patent is extended or adjusted under 35 U.S.C. 154(b) by 144 days.

(21) Appl. No.: 14/187,359

(22) Filed: Feb. 24, 2014

(65) Prior Publication Data
US 2015/0244344 A1    Aug. 27, 2015

(51) Int. Cl.
| | |
|---|---|
| *H03H 9/125* | (2006.01) |
| *H01L 41/09* | (2006.01) |
| *H03H 9/25* | (2006.01) |
| *G01M 15/14* | (2006.01) |
| *F01D 17/02* | (2006.01) |
| *F01D 21/00* | (2006.01) |
| *G01K 1/02* | (2006.01) |
| *H04Q 9/00* | (2006.01) |
| *G01N 29/24* | (2006.01) |

(52) U.S. Cl.
CPC ............... *H03H 9/25* (2013.01); *F01D 17/02* (2013.01); *F01D 21/003* (2013.01); *G01K 1/024* (2013.01); *G01M 15/14* (2013.01); *G01N 29/2462* (2013.01); *H04Q 9/00* (2013.01); *F05D 2230/90* (2013.01); *G01N 2291/2693* (2013.01)

(58) Field of Classification Search
USPC .................................................. 310/311–371
See application file for complete search history.

(56) References Cited

U.S. PATENT DOCUMENTS

| | | | |
|---|---|---|---|
| 4,379,226 A * | 4/1983 | Sichling | G01D 5/268 250/231.1 |
| 8,033,722 B2 | 10/2011 | Kulkarni et al. | |
| 8,052,324 B2 | 11/2011 | Gregory et al. | |
| 8,132,467 B2 | 3/2012 | Shinde et al. | |
| 8,151,623 B2 | 4/2012 | Shinde et al. | |
| 2006/0273904 A1* | 12/2006 | Funo | G03G 15/50 340/572.1 |
| 2008/0088201 A1* | 4/2008 | Konishi | G06K 7/10009 310/313 D |
| 2010/0117859 A1 | 5/2010 | Mitchell et al. | |
| 2011/0280279 A1 | 11/2011 | Gregory et al. | |
| 2014/0052410 A1 | 2/2014 | Tralshawala et al. | |

FOREIGN PATENT DOCUMENTS

| | | |
|---|---|---|
| CH | 701486 A2 | 1/2011 |
| EP | 2458150 A1 | 5/2012 |
| EP | 2816200 A1 | 12/2014 |
| WO | WO2007130862 A2 | 11/2007 |

* cited by examiner

*Primary Examiner* — Thomas Dougherty

(57) ABSTRACT

A self-powered sensing and transmitting circuit (50) including a power element (44) and a sensing element (46) that is powered by the power element for generating a sensor signal responsive to a local operating environment The circuit also includes a transmitting element (48) powered by the power element for transmitting an output signal responsive to the sensor signal to a receiving location (33, 55) remote from the circuit The power element, sensing element and transmitting element of the circuit are arranged in a generally planar and non-integrated circuit configuration formed on a substrate (57) component exposed to operating temperatures at or exceeding 650° C.

20 Claims, 2 Drawing Sheets

SELF-POWERED SENSING AND TRANSMITTING DEVICE AND METHOD OF FABRICATING THE SAME

FIELD OF THE INVENTION

The present invention relates generally to monitoring parameters of operating environments, such as within an operating combustion environment of a gas turbine engine More specifically, the present invention relates to wireless telemetry systems for monitoring operating parameters of turbine components

BACKGROUND OF THE INVENTION

Gas combustion turbines are used for a variety of application such as driving an electric generator in a power generating plant or propelling a ship or an aircraft Firing temperatures in modern gas turbine engines continue to increase in response to the demand for higher efficiency engines Superalloy materials have been developed to withstand the corrosive high temperature environment that exists within a gas turbine engine However, even superalloy materials are not able to withstand extended exposure to the hot combustion gas of a current generation gas turbine engine without some form of cooling and/or thermal insulation.

Thermal barrier coatings are widely used for protecting various hot gas path components of a gas turbine engine The reliability of such coating is critical to the overall reliability of the machine The design limits of such coatings are primarily determined by laboratory data However, validation of thermal barrier coating behavior is essential for a better understanding of the coating limitations Such real world operating environment data is very difficult to obtain, particularly for components that move during the operation of the engine, such as the rotating blades of the turbine.

Despite the extreme sophistication of modern turbine engines, such as gas turbines for generating electrical power or aircraft engines for commercial and military use, designers and operators have very little information regarding the internal status of the turbine engine components during operation This is due to the harsh operating conditions, which have prevented the use of traditional sensors for collecting reliable information of critical engine components There is an increasing demand for real-time structural health monitoring and prognostics of critical components in current turbine engines to meet the demanding requirements of the future Wireless telemetry systems including power supplies, sensors and transmitters are known, however, the harsh turbine environments encountered in the turbine engines along with the lack of long-term demonstrated sensor functionality, together with incapable signal transmission from hot sections render it difficult to meet the desired objectives Efforts have been carried out to demonstrate wireless telemetry capabilities for strain and temperature sensing, however, it is limited by the capability of the wireless transmitting package for gas turbine operating temperatures in excess of 500° C.

MEMS devices or sensors have been used or at least attempts have been made to MEMS devices in connection with systems for monitoring operating parameters of turbine components Such devices are integrated circuits that are fabricated and then mounted to a component substrate, however, the wireless telemetry packages have limited capabilities in gas turbine relevant conditions Surface acoustic wave (SAW) devices are passive devices that sense a property in their region, i e temperature, strain, pressure, vibration, etc The device is interrogated by an antennae located a distance away, and when interrogated, the SAW device uses the interrogation pulse, powers up, and transmits its data SAW devices are typically fabricated from processes such as photolithography, ink jet printing, photoresist removal, and densification via thermal or laser methods Processes that include sintering and/or densification result in shrinkage and increasing material strain and limit the types of materials that can be processed to full density, without undergoing structural damage The materials that can be processed using such techniques limit the operation of the devices to about 600° C. In addition, the SAW devices must be attached to the component surface The attachment techniques used also limit operation of conventional high temperature SAW devices to less than 600° C.

Other methods for depositing high temperature capable materials as SAW devices might be used, such as chemical vapor deposition (CVD) and physical vapor deposition (PVD) techniques, such as pulsed laser deposition. However, these processes are limited in the compositions of materials they may produce, are very expensive to perform, and are limited in the size of component on which they may deposit devices High temperature SAW devices have been demonstrated by few companies using metal or metal based composite systems, however, their performance has been demonstrated at temperatures up to about 650° C. for only a few hundred hours Previously issued patents U.S. Pat. Nos. 8,033,072, 8,132, 467, and 8,151,623 disclose thermocouple, strain gauge and wear sensors and connectors for use in temperatures exceeding 1200° C. that can be fabricated using thermal spray and masking technologies. However, the inventors of the subject invention are not aware of thermal spray and masking technologies being used to form thin film devices that are operable in temperatures exceeding 650° C. and up to about 1500° C.

BRIEF DESCRIPTION OF THE DRAWINGS

The invention is explained in the following description in view of the drawings that show

DETAILED DESCRIPTION OF THE INVENTION

Figure 1:
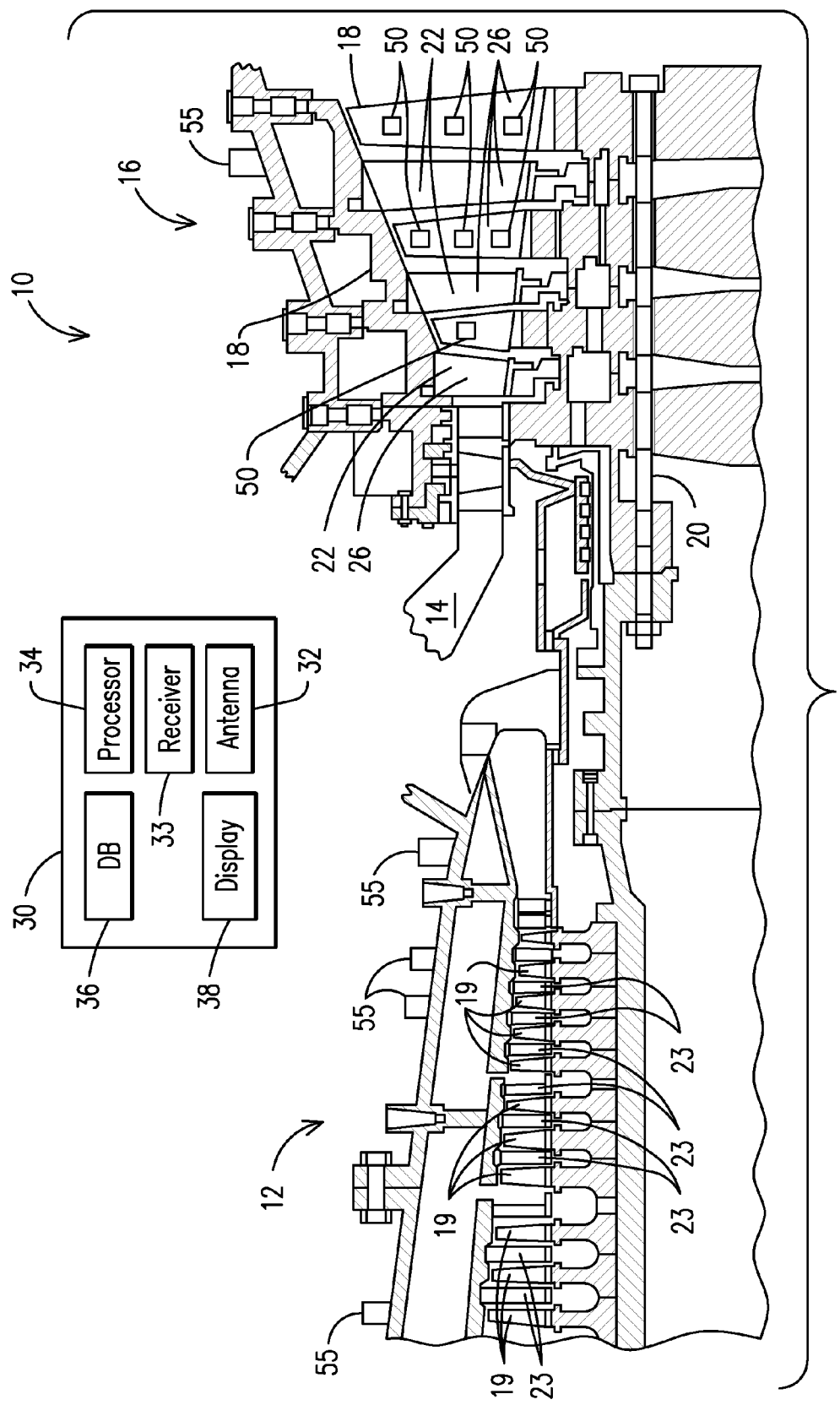
FIG. 1 is a cross sectional view of an exemplary combustion turbine with which embodiments of the invention may be used and an exemplary monitoring and control system for collecting and analyzing component data from the combustion

In response to long-felt need for improved real-time diagnostic data for machines such as gas turbine engines, the present inventors have innovatively developed a self-powered, sensing and transmitting circuit that can be placed within an operating environment, such as by being applied to a gas turbine engine component, in order to sense the local operating environment and to deliver real-time operating environment data to a location outside of the environment Such a device may include a power element, a sensing element powered by the power element for generating a sensor signal responsive to the local operating environment, and a transmitting element powered by the power element for transmitting, to a receiving location remote from the device, an output signal responsive to the sensor signal In an embodiment of the invention, the device is a sound acoustic wave (SAW) device that may include a thermoelectric power generation element, input and output interdigitated transducers and an antenna for transmission of data to a remotely positioned receiver Such a device may be fabricated preferably from known plasma spray and/or thermal spray and masking techniques using materials that are functional in operating temperatures of up to about 1500° C. or greater The device is developed or fabricated as a generally planar circuit and without an integrated configuration and covers a relatively large surface on the component with minimal, if any, effect to the aerodynamics of a hot gas path of a turbine engine Thus the term planar as used to describe circuitry of such a self-powered sensing and transmission device may mean circuits or circuitry that is arranged in a linear, non-integrated configuration The size of such circuitry is such that masking and spray technologies are capable of being used to fabricate the device For example, devices having area sizes larger than 50 microns may be effectively fabricated from masking and thermal spray techniques to form such a planar circuitry The other advantage of the spray technique is the ability to deposit the circuitry conformal to the surface of the component which enables the monitoring everywhere on the component (for e g leading edge, trailing edge, platforms) where distress issues occur FIG. 1 illustrates an exemplary combustion turbine 10 such as a gas turbine used for generating electricity as will be recognized by those skilled in the art Embodiments of the invention may be used with combustion turbine 10 or in numerous other operating environments and for various purposes as will be recognized by those skilled in the art For example, embodiments may be used in aircraft engines, monitoring temperature and heat flux in boilers, heat exchangers and exhaust stacks; determining insulation performance and degradation, determining pipe fouling, and evaluating vibrating component health Embodiments may be used in the automotive industry for monitoring combustion chamber conditions, rotating components such as crankshaft, cams, transmissions and differentials, and determining suspension and frame integrity for heavy-duty vehicles Embodiments may also be used in measuring strain and heat flux in tanks, portable and other equipment operating in dessert, wet, and/or high temperature configurations Returning to FIG. 1, combustion turbine 10 includes a compressor 12, at least one combustor 14 (broken away) and a turbine 16 Compressor 12, combustor 14 and turbine 16 are sometimes referred to collectively as a gas turbine engine Turbine 16 includes a plurality of rotating blades 18, secured to a rotatable central shaft 20 A plurality of stationary vanes 22 are positioned between blades 18, with vanes 22 being dimensioned and configured to guide air over blades 18 Blades 18 and vanes 22 will typically be made from nickel-cobalt, and may be coated with a thermal barrier coating 26, such as yttria-stabilized zirconia Similarly, compressor 12 includes a plurality of rotating blades 19 positioned between respective vanes 23

In use, air is drawn in through compressor 12, where it is compressed and driven towards combustor 14 Combustor 14 mixes the air with fuel and ignites it thereby forming a working gas This working gas will typically be above 1300° C. This gas expands through turbine 16, being guided across blades 18 by vanes 22 As the gas passes through turbine 16, it rotates blades 18 and shaft 20, thereby transmitting usable mechanical work through shaft 20 Combustion turbine 10 may also include a cooling system (not shown), dimensioned and configured to supply a coolant, for example steam or compressed air, to blades 18 and vanes 22

Figure 2:
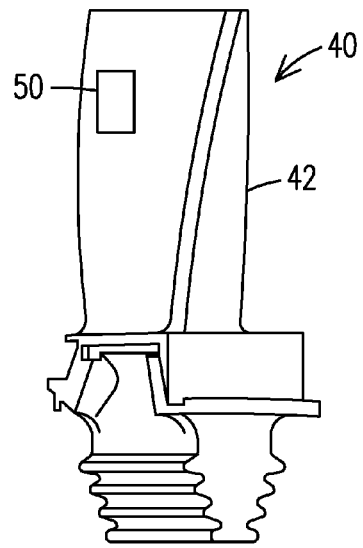
FIG. 2 is perspective view of an embodiment of a smart component of a gas turbine engine in accordance with aspects of the invention
Figure 3:
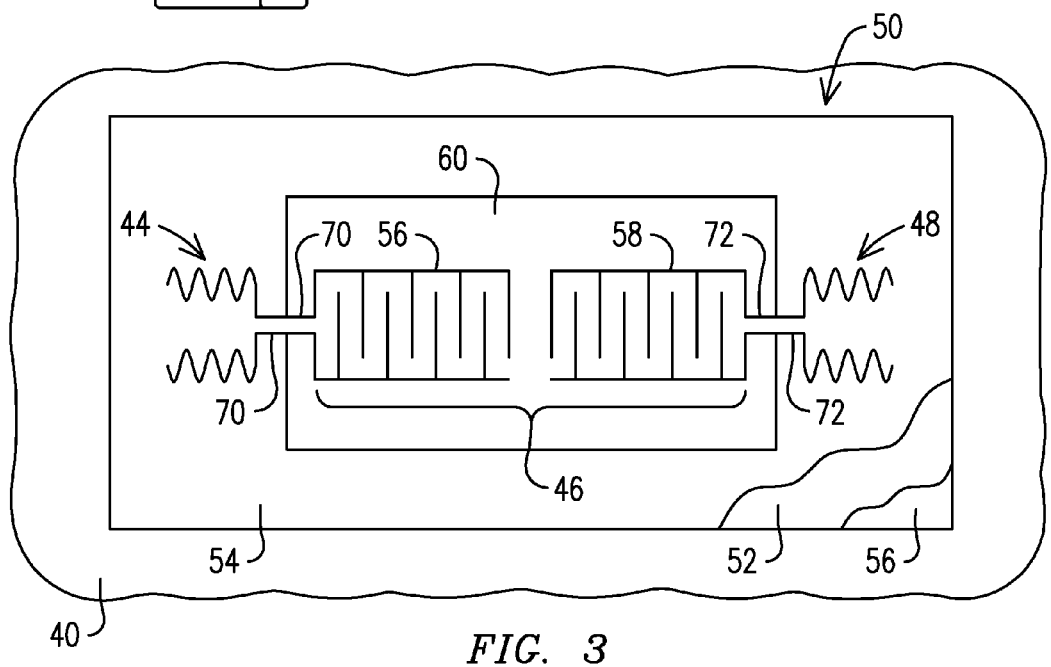
FIG. 3 is a schematic illustration of a self-powered sensor and transmitting device in accordance with aspects of the invention
Figure 4:
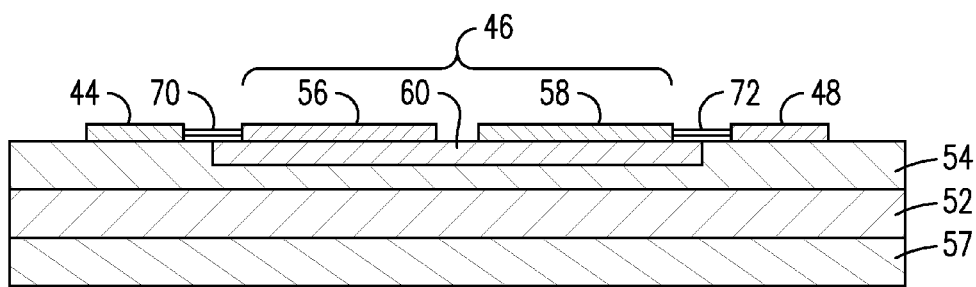
FIG. 4 is a schematic sectional view of device of self-powered sensor and transmitting device of FIG. 3 on a turbine component substrate

The environment wherein blades 18 and vanes 22 operate is subject to high operating temperatures and is particularly harsh, which may result in serious deterioration of blades 18 and vanes 22 This is especially likely if the thermal barrier coating 26 should spall or otherwise deteriorate Embodiments of the invention are advantageous because they allow components to be configured for transmitting data indicative of a component's condition during operation of combustion turbine 10 Blades 18, 19, vanes 22, 23, and coatings 26, for example, may be configured for transmitting component specific data that may be directly monitored to determine the respective condition of each component during operation and to develop predictive maintenance schedules FIG. 1 also illustrates a schematic of an exemplary monitoring and control system 30 that may be used in accordance with various aspects of the present invention. System 30 may include an antenna 32, a receiver 33, a processor or CPU 34, a database 36 and a display 38 Processor 34, database 36 and display 38 may be conventional components and antenna 32 and receiver 33 may have performance specifications that are a function of various embodiments of the invention For example, antenna 32 and receiver 33 may be selected for receiving wireless telemetry data transmitted from a plurality of transmitters deployed in various locations throughout combustion turbine 10 as more fully described below A self-powered sensing and transmission device 50 is shown schematically on a turbine blade 40 in FIG. 2, and the components of the device 50 are schematically shown in FIG. 3 As illustrated in FIG. 2, the device 50 may be attached to the airfoil 42 of the blade 40, or any other area on the blade 40 that requires monitoring of operating parameters of the blade 40 and/or turbine machine 10. Examples of operating parameters that may be monitored include the temperature of hot gas path across the blade, the strain on the component and/or vibration of the component As further shown in FIGS. 3 and 4, the device includes a power generation element 44, a sensing element 46 and one or transmission elements 48, which may function as a transceiver to transmit and receive signals. The airfoil 42 includes a substrate 57 made of a superalloy such as a Ni based superalloy that is coated with a thermal barrier coating (TBC) 52 A dielectric layer 54 is disposed on the airfoil 42 between the TBC 52 and the components 44, 46 and 48

The components 44, 46 and 48 and dielectric layer 52 may formed using known spray and/or deposition techniques such as plasma spraying, electron beam (EB) deposition, physical vapor deposition (PVD) chemical vapor deposition (CVD), pulsed laser deposition, mini-plasma, direct-write, mini-high velocity oxyfuel (hvof) or solution plasma spraying In a preferred method of manufacturing an instrumented component a thermal spray technique may be used for depositing the different components of the device 50 onto the substrate 57 and/or TBC 52

Embodiments of the present invention may be powered by various means such as induced RF energy and/or by harvesting thermal or vibrational power within the combustion turbine engine 16 In the energy harvested power model, either thermoelectric or vibro-electric power could be generated from the energy available in an operating combustion turbine engine 16 Thermopiles may be used to generate electricity from thermal energy, or piezoelectric materials may generate electricity from vibration of combustion turbine engine 16

Examples of these forms of power sources are described in U.S. Pat. No. 7,368,827, the entire disclosure of which is incorporated herein by reference Accordingly, the power generation component 44 may be a thermocouple or thermopile configured to generate power harvested from the heat energy generated in the turbine machine The thermopile could be made of known ceramic and metallic materials which can be deposited using any one of the above listed deposition techniques In an embodiment, the materials may generate power up to about 3 mV or greater and can operate in temperatures of up to about 1200° C. Such materials may include mono-elemental oxides such as ZnO and/or InO or some transparent conducting oxides like Indium tin oxide or thermoelectric oxides like Zinc ferrite or Calcium ferrite The sensing element 46 is preferably a sound acoustic wave (SAW) device that includes an input interdigital transducer 56 and an output interdigital transducer 58 formed on a piezoelectric substrate 60 As in a typical SAW device a line delay 59 or gap is between the transducers 56, 58 One or more electrical leads 70 provides electrical communication with the power element 44 and the input transducer 56 and one or more electrical leads 72 provides electrical communication between the output transducer 58 and the transmission element 48 The piezoelectric substrate 60 may be composed of a piezoelectric material such as ordered langasite $A_3BC_3D_2O_{14}$ structure, which can function at temperature of up to about 1500° C. Some compositions include $Sr_3TaGa_3Sl_2O_{14}$, $Sr_3NbGa_3Si_2O_{14}$, $Ca_3TaGa_3Sl_2O_{14}$ and $Ca_3TaAl_3Sl_2O_{14}$. The thermal barrier coating 52 may be composed of a ceramic material like zirconates or hafniates, for e g yttrium stabilized zirconia, able to function in gas temperatures of up to about 1500° C. or greater. The dielectric layer may be composed an aluminate material, such as yttrium aluminum garnett (YAG) and/or aluminum oxide ($Al_2O_3$), which is functional at temperatures of up to about 1400° C. Lead wires, electrical contacts and components of the transducers 56, 58 may be composed precious metals such as platinum and/or palladium, which may be operational at temperatures up to about 1500° C.

A mentioned above, an embodiment the SAW device and its components may be formed using thermal spray deposition and masking techniques, known to those skilled in the art The performance of the materials are optimized through process parameter development during the spray process, these include gas flows, gun current, powder flow Materials that can be used for masking may include metallic or polymeric materials that are dimensioned to generally conform to the surface topography or shape of the substrate and TBC Such materials may include graphite or copper foils, aluminum and steel tapes. Post processing steps such as laser etching may be used to refine the components of the sensor 50

The device 50 including it components may formed by first depositing an electrically insulating layer such as the dielectric layer or substrate 52 on to the component substrate 57. To the extent the substrate 57 includes a TBC, the dielectric layer 54 is formed on the TBC 52 Prior to depositing the dielectric layer 54 onto the TBC 52 or 57, a mask configured and dimensioned for the dielectric layer 52 may be established on the substrate 57 and/or TBC 52

After the dielectric layer 54 is formed, masking and deposition steps are performed sequentially to form the remaining components on the dielectric layer For example, a mask configured for the deposition of the piezoelectric substrate 60 is placed over the dielectric layer 54 and a material such as langasite is thermally sprayed on to the dielectric layer 54. Following deposition of the piezoelectric substrate 60, masking is provided for the deposition of the transducers 56, 58 and the electrical components making up the transducers 56, 58, as well for the power element 44 and the transmission element 48.

Again in reference to FIG. 1, the system 30 includes one or more transceivers 55 located at different positions on the casing of the turbine machine for the wireless transmission of interrogating signals to the self-powered sensing and transmission devices 50 Upon receipt of an interrogating sign at the antenna 48, the power element 44 is activated to power the sensing element 46 and transmission element 48 Accordingly, the sensing element generates one or more signals indicative of the monitored parameter such as temperature, strain and vibration, for example, and the transmission element is configured to transmit one or more signals indicative of the operating parameter to the remote transceivers 55 In an embodiment, the transceivers 55 are configured to transmit data signals to system 30 for recordation and analysis of the turbine machine 10 and its components based on the data generated by device 50 For a device on 50 on a rotating turbine blade 40, the device 50 may be interrogated at various different locations or positions during rotation of the blade 40 about shaft 20 In addition, or alternatively, the device 50 may be configured so that the power element 44 generates power transmitted to the sensing element 46 at predetermined timed intervals so that operating parameter data is generated and transmitted at these predetermined timed intervals without the need of interrogation While various embodiments of the present invention have been shown and described herein, it will be obvious that such embodiments are provided by way of example only Numerous variations, changes and substitutions may be made without departing from the invention herein. Accordingly, it is intended that the invention be limited only by the spirit and scope of the appended claims.

The invention claimed is:

1. A self-powered sensing and transmitting circuit, comprising:
    a power element;
    a sensing element powered by the power element for generating a sensor signal responsive to a local operating environment;
    a transmitting element powered by the power element for transmitting an output signal responsive to the sensor signal to a receiving location remote from the circuit; and
    wherein the power element, sensing element and transmitting element are arranged in a generally planar and non-integrated circuit configuration and formed on a substrate component configured to operate at temperatures at or exceeding 650° C.

2. The circuit of claim 1 further comprising:
    a dielectric layer other than the substrate component;
    a piezoelectric substrate formed on the dielectric layer; and
    wherein the sensing element is formed on the piezoelectric substrate.

3. The circuit of claim 1 wherein the power generating element is a thermoelectric power generating element.

4. The circuit of claim 3 wherein the power generating element is a thermocouple.

5. The circuit of claim 2 wherein the sensing element comprises:
    an input interdigital transducer formed on the piezoelectric substrate in electrical communication with the power element; and an output interdigital transducer formed on the piezoelectric substrate and in electrical communication with the transmitting element wherein the generally planar configuration is a linear configuration of the input interdigital transducer, the power element, the output interdigital transducer and the transmitting element along a surface of the piezoelectric substrate opposite from the dielectric layer.

6. A circuit comprising:
a component substrate;
a power element;
a sensing element powered by the power element for generating a sensor signal responsive to a local operating environment;
a transmitting element powered by the power element for transmitting an output signal responsive to the sensor signal to a receiving location remote from the from the component substrate; and
wherein the power element, sensing element and transmitting element are arranged in a generally planar and non-integrated circuit configuration along a surface of the component substrate and the component and component substrate are configured to operate in an environment having operating temperatures exceeding 650° C.

7. The circuit of claim 6 further comprising:
a dielectric layer other than the component substrate;
a piezoelectric substrate formed on the dielectric layer; and,
wherein the sensing element is formed on a side of the piezoelectric substrate opposite to the dielectric layer.

8. The circuit of claim 6 wherein the power generating element is a thermoelectric power generating element.

9. The circuit of claim 8 wherein the power generating element is a thermocouple.

10. The circuit of claim 7 wherein the sensing element comprises:
an input interdigital transducer formed on the piezoelectric substrate in electrical communication with the power element; and,
an output interdigital transducer formed on the piezoelectric substrate and in electrical communication with the transmitting element.

11. The circuit of claim 1 wherein the planar and non-integrated circuit configuration is formed with spraying and masking techniques.

12. The circuit of claim 1 further comprising a dielectric layer on the substrate component, wherein the planar circuit configuration is a linear configuration of the power element, the sensing element and the transmitting element along a side of the dielectric layer opposite from the substrate component.

13. The circuit of claim 1, wherein the power element is made from a mono-elemental oxide material.

14. The circuit of claim 2, wherein the dielectric layer is formed of an aluminate material and wherein the piezoelectric substrate is formed of ordered langasite material.

15. The circuit of claim 2, further comprising a thermal barrier coating between the dielectric layer and the substrate component, wherein the thermal barrier coating is formed of at least one of zirconate and hafniate material.

16. A component of a gas turbine engine comprising the circuit of claim 1 formed on a substrate of the component.

17. The component of claim 16, wherein the component is one of a blade and vane within a turbine of the gas turbine engine and wherein the sensor signal is responsive to at least one of a temperature of a hot gas path within the turbine across the component, a strain on the component, and a vibration of the component.

18. The component of claim 17, wherein component is an airfoil of the blade within the turbine of the gas turbine engine, wherein the substrate is coated with a thermal barrier coating (TBC) and wherein a dielectric layer is disposed on the airfoil between the TBC and the power element, sensing element and transmitting element.

19. The component of claim 16, further comprising at least one transceiver located at a position along the gas turbine engine for wireless transmission of an interrogating signal to the circuit such that the circuit is configured to generate the sensor signal including data of a monitored parameter of the component of the gas turbine engine in response to the interrogating signal.

20. The component of claim 19, wherein the component is an airfoil of a blade within a turbine of the gas turbine engine and wherein the monitored parameter is one of temperature of a hot gas path within the turbine across the airfoil, a strain on the airfoil and a vibration of the airfoil within the turbine.

* * * * *